(12) United States Patent  (10) Patent No.: US 6,685,734 B1
Välimaa et al.  (45) Date of Patent: Feb. 3, 2004

(54) URETHRAL STENT DELIVERY SYSTEM

(75) Inventors: Tero Välimaa, Tampere (FI); Martti Talja, Lahti (FI); Pertti Törmälä, Tampere (FI)

(73) Assignee: Linvatec Biomaterials Oy, Tampere (FI)

( * ) Notice: Subject to any disclaimer, the term of this patent is extended or adjusted under 35 U.S.C. 154(b) by 0 days.

(21) Appl. No.: 09/465,789

(22) Filed: Dec. 17, 1999

(51) Int. Cl.$^7$ .................................................. A61F 2/06
(52) U.S. Cl. ....................................................... 623/1.11
(58) Field of Search .......................... 623/1.11, 1, 1.23; 606/198, 108, 191–195, 200; 604/96.01, 101.01, 103.05, 919–921, 915–917

(56) References Cited

U.S. PATENT DOCUMENTS

| | | |
|---|---|---|
| 4,512,338 A | 4/1985 | Balko et al. |
| 4,531,933 A | 7/1985 | Norton et al. |
| 4,713,049 A | 12/1987 | Carter |
| 4,790,810 A | 12/1988 | Pugh et al. |
| 4,813,925 A | 3/1989 | Anderson, Jr. et al. |
| 4,820,262 A | 4/1989 | Finney |
| 4,820,298 A | 4/1989 | Leveen et al. |
| 4,822,333 A | 4/1989 | Lavarenne |
| 4,922,905 A | 5/1990 | Strecker |
| 4,932,958 A | 6/1990 | Reddy et al. |
| 4,950,227 A | 8/1990 | Savin et al. |
| 4,969,458 A | 11/1990 | Wiktor |
| 4,973,301 A | 11/1990 | Nissenkorn |
| 5,007,898 A | 4/1991 | Rosenbluth et al. |
| 5,030,227 A | 7/1991 | Rosenbluth et al. |
| 5,098,374 A | 3/1992 | Othel-Jacobsen et al. |
| 5,160,341 A | 11/1992 | Brenneman et al. |
| 5,209,725 A | 5/1993 | Roth |
| 5,263,931 A | 11/1993 | Miller |
| 5,304,214 A | 4/1994 | DeFord et al. |
| 5,322,501 A | 6/1994 | Mahmud-Durrani |
| 5,667,486 A | 9/1997 | Mikulich et al. |
| 5,752,971 A | 5/1998 | Rosenbluth et al. |
| 5,766,204 A | 6/1998 | Porter et al. |

FOREIGN PATENT DOCUMENTS

| | | |
|---|---|---|
| DE | 28 27 908 | 1/1980 |
| EP | 0 543 309 | 11/1995 |
| EP | 0 753 289 | 1/1997 |
| EP | 0 873 760 | 10/1998 |

*Primary Examiner*—Michael J. Milano
*Assistant Examiner*—(Jackie) Tan-Uyen T. Ho
(74) *Attorney, Agent, or Firm*—Kenyon & Kenyon

(57) ABSTRACT

A device for inserting a stent in a body cavity, particularly useful for inserting a stent into a human male urethra to treat prostatic hyperplasia, whereby such device has an elongated member for removably receiving a stent and means capable of protruding from the member to either locate an obstruction, such as the sphincter muscle, in the body cavity or to prevent the stent from sliding off of the member, or both.

10 Claims, 12 Drawing Sheets

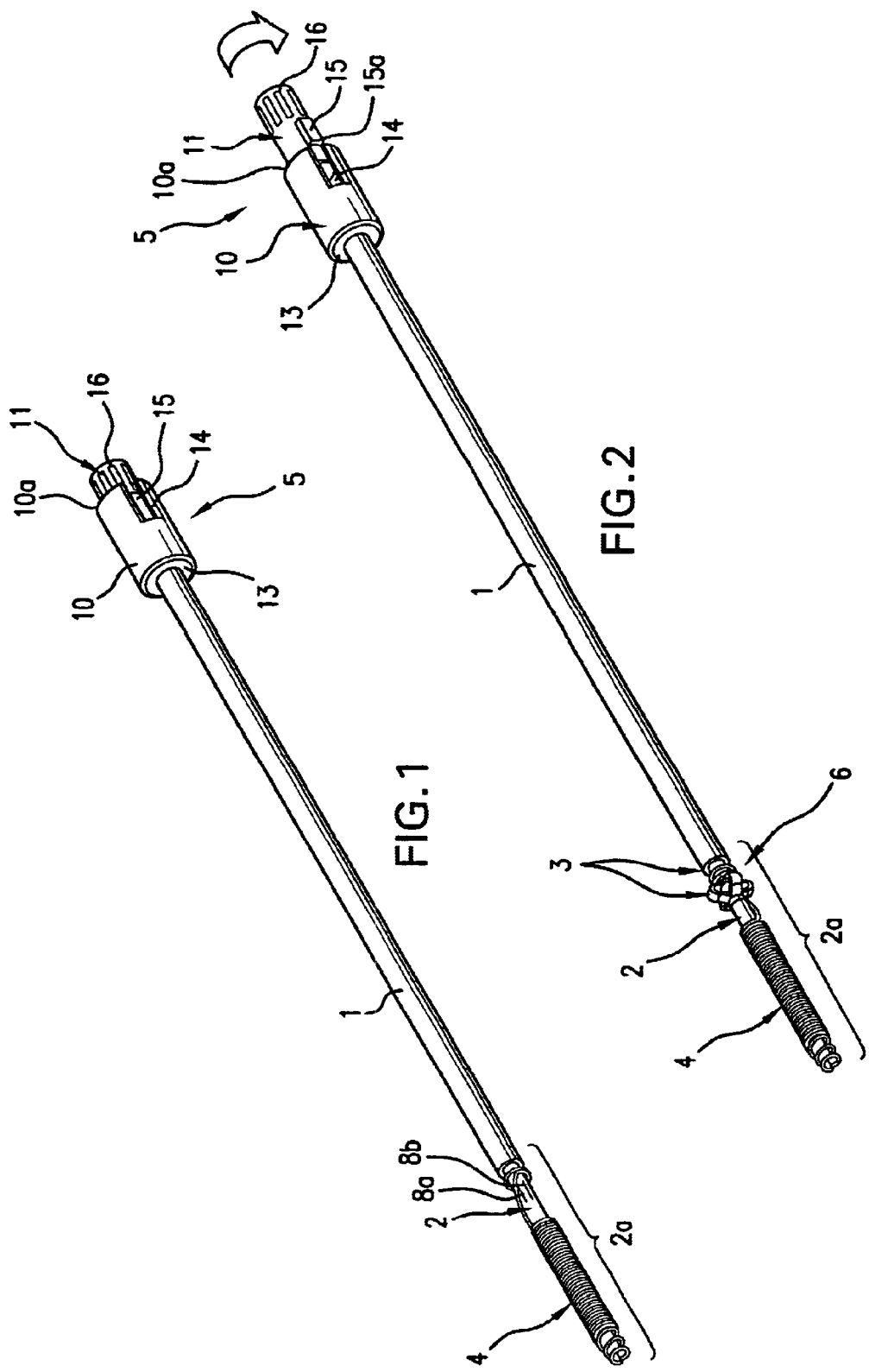

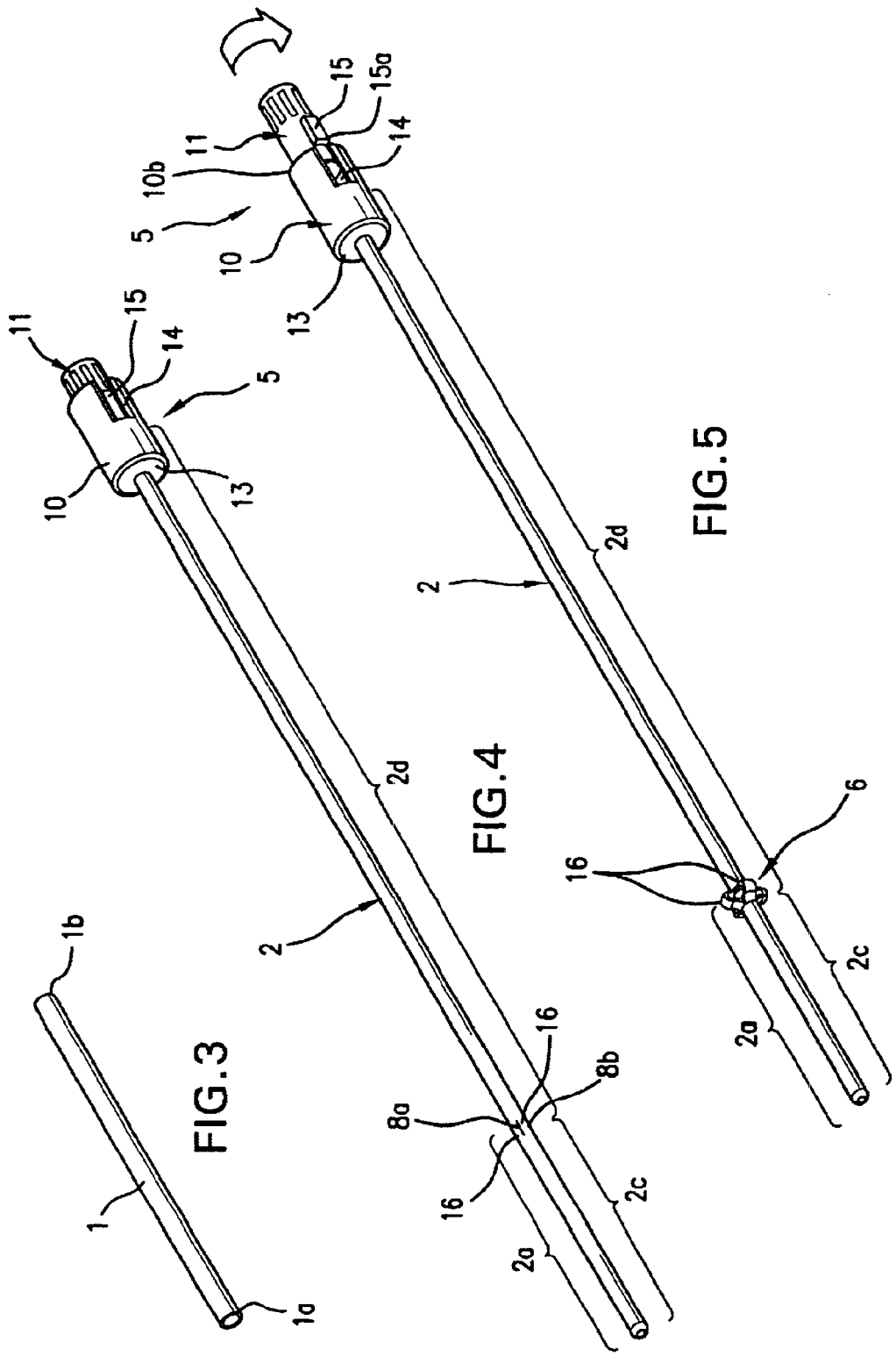

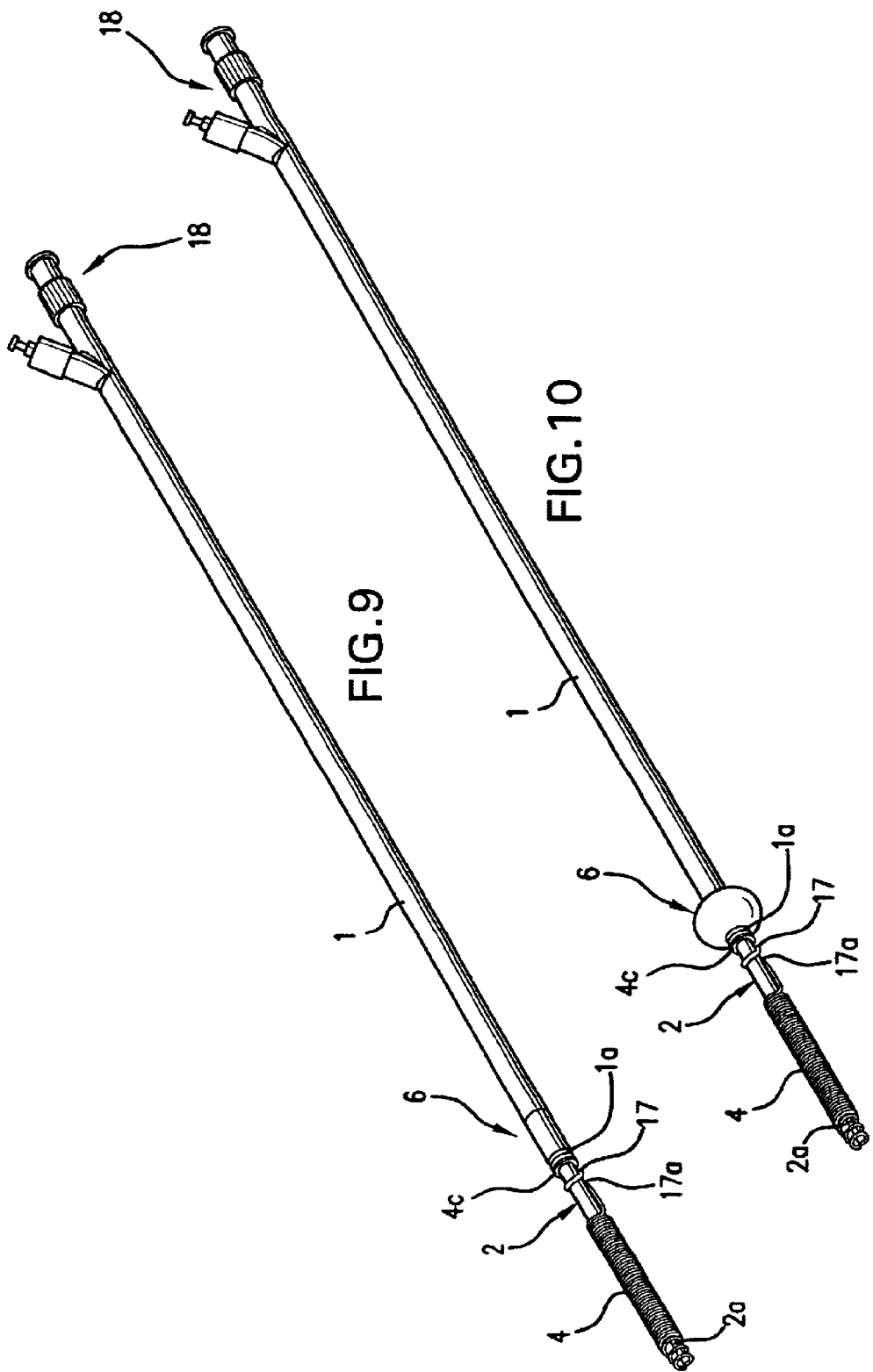

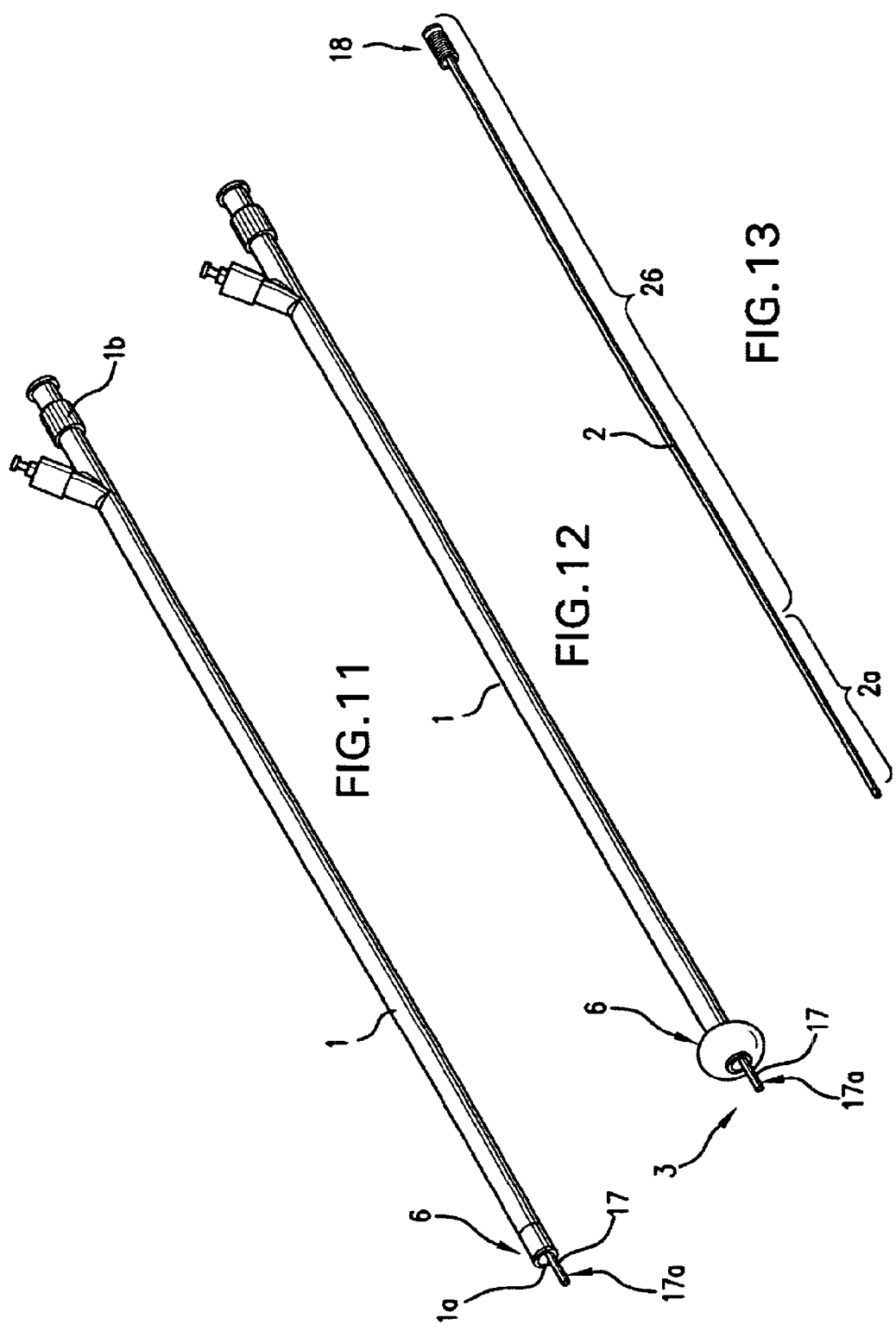

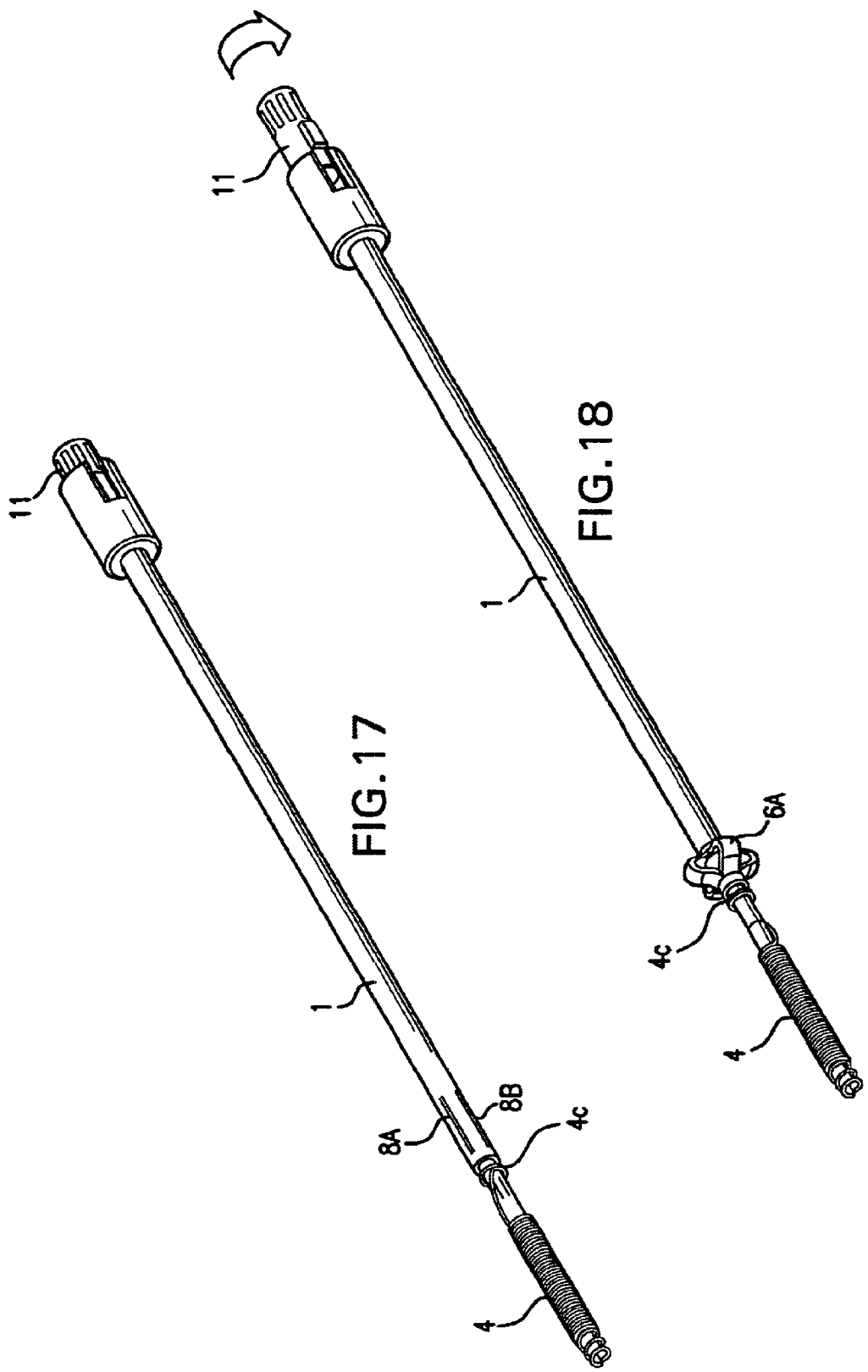

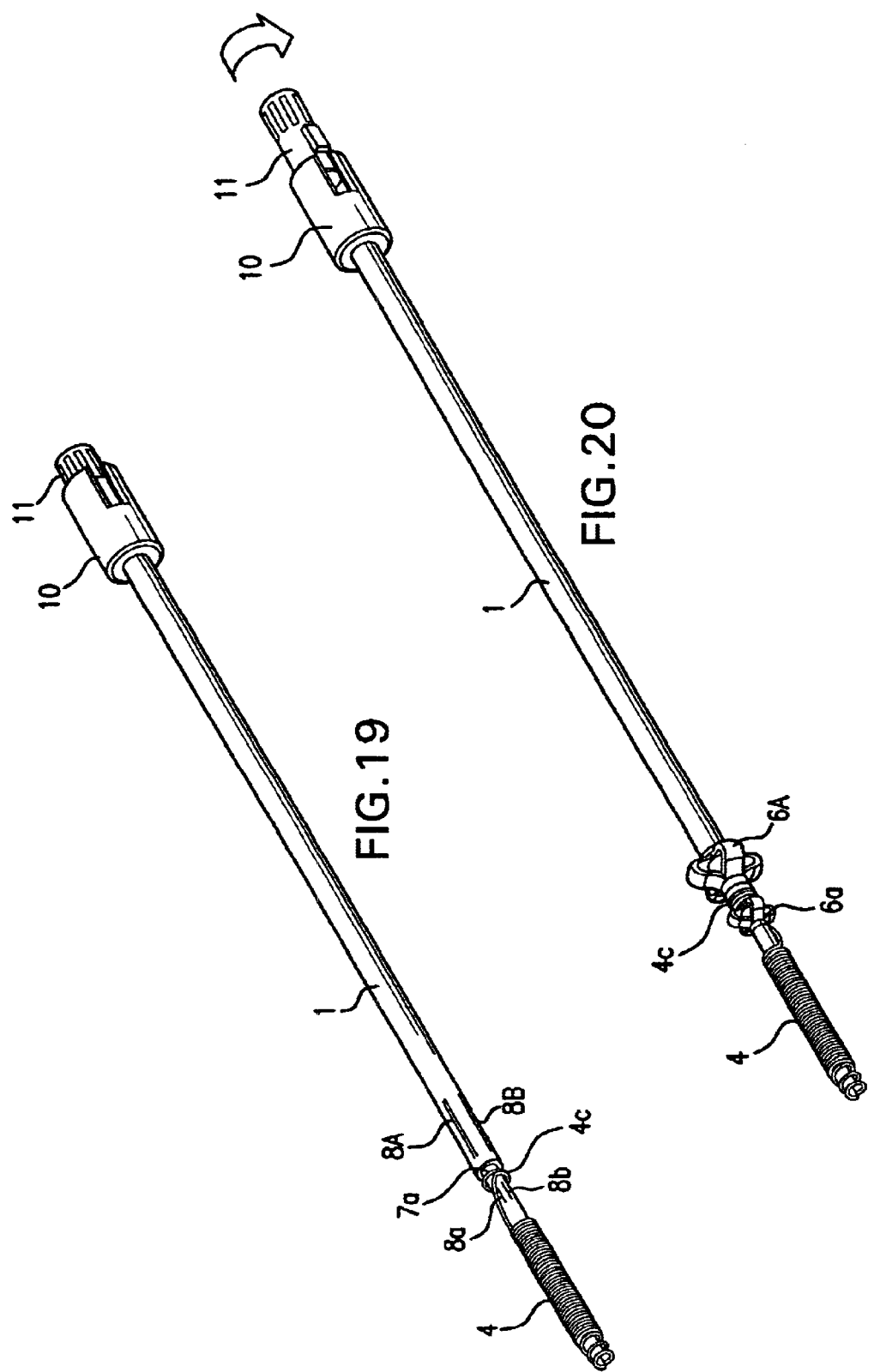

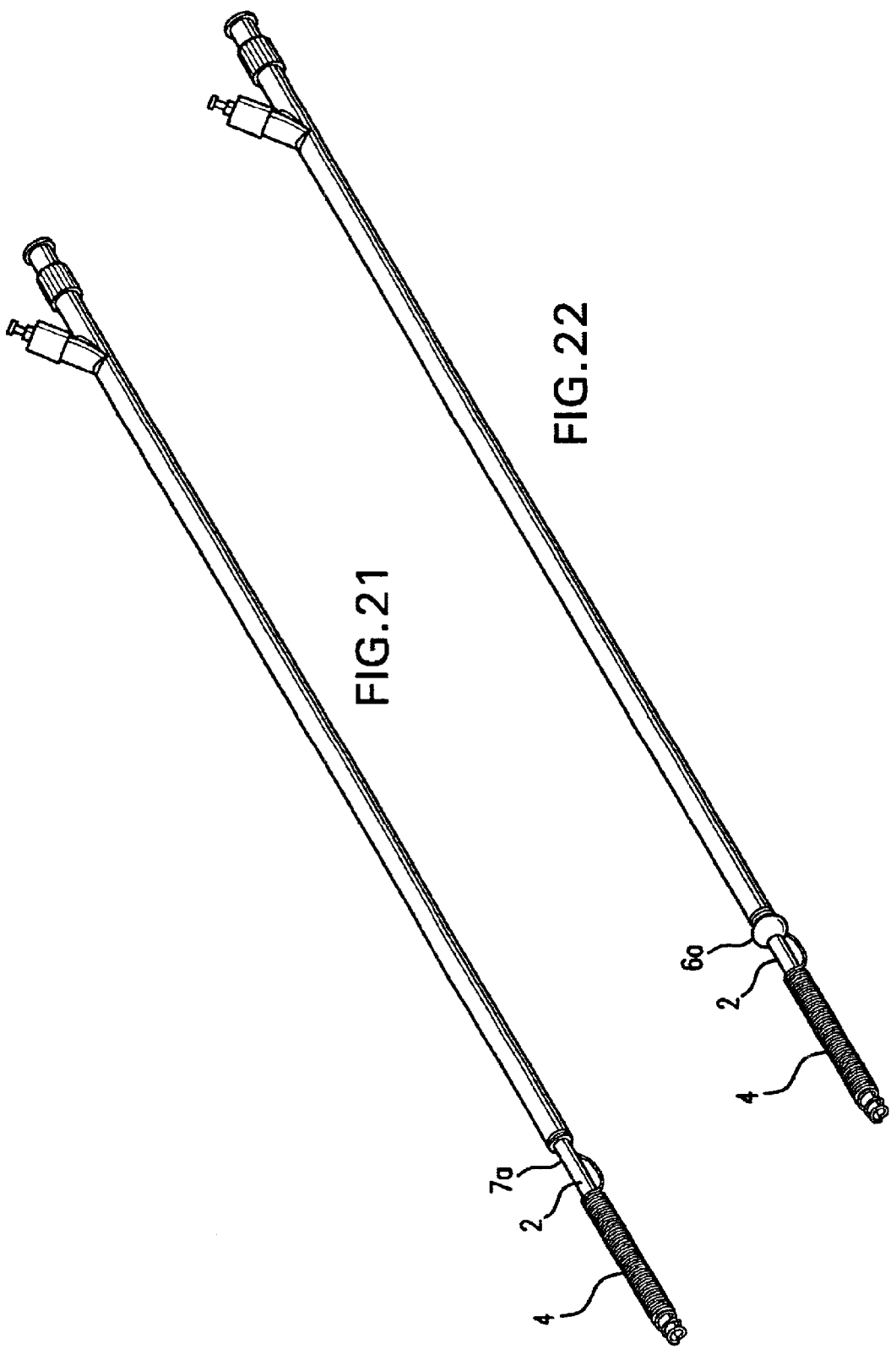

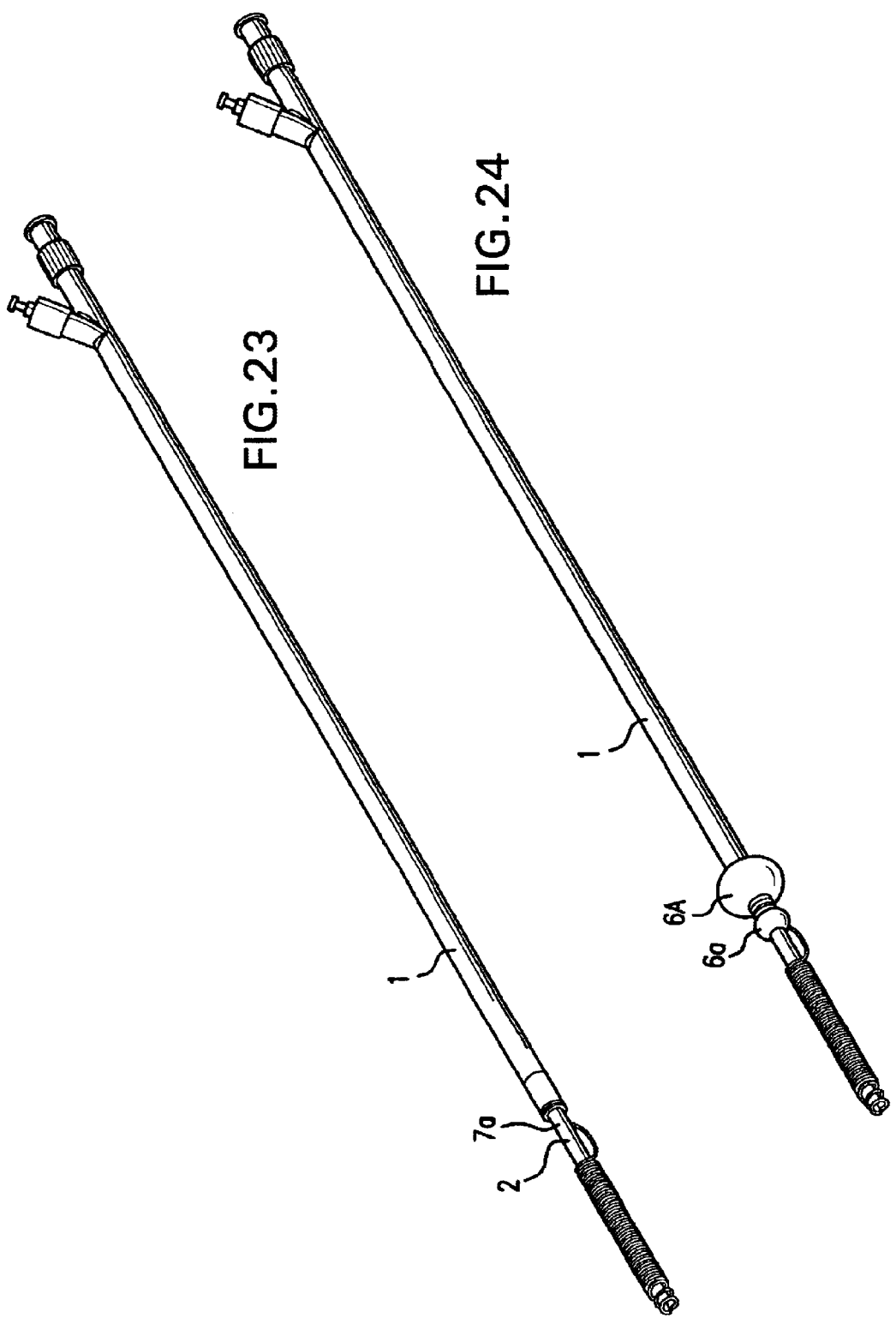

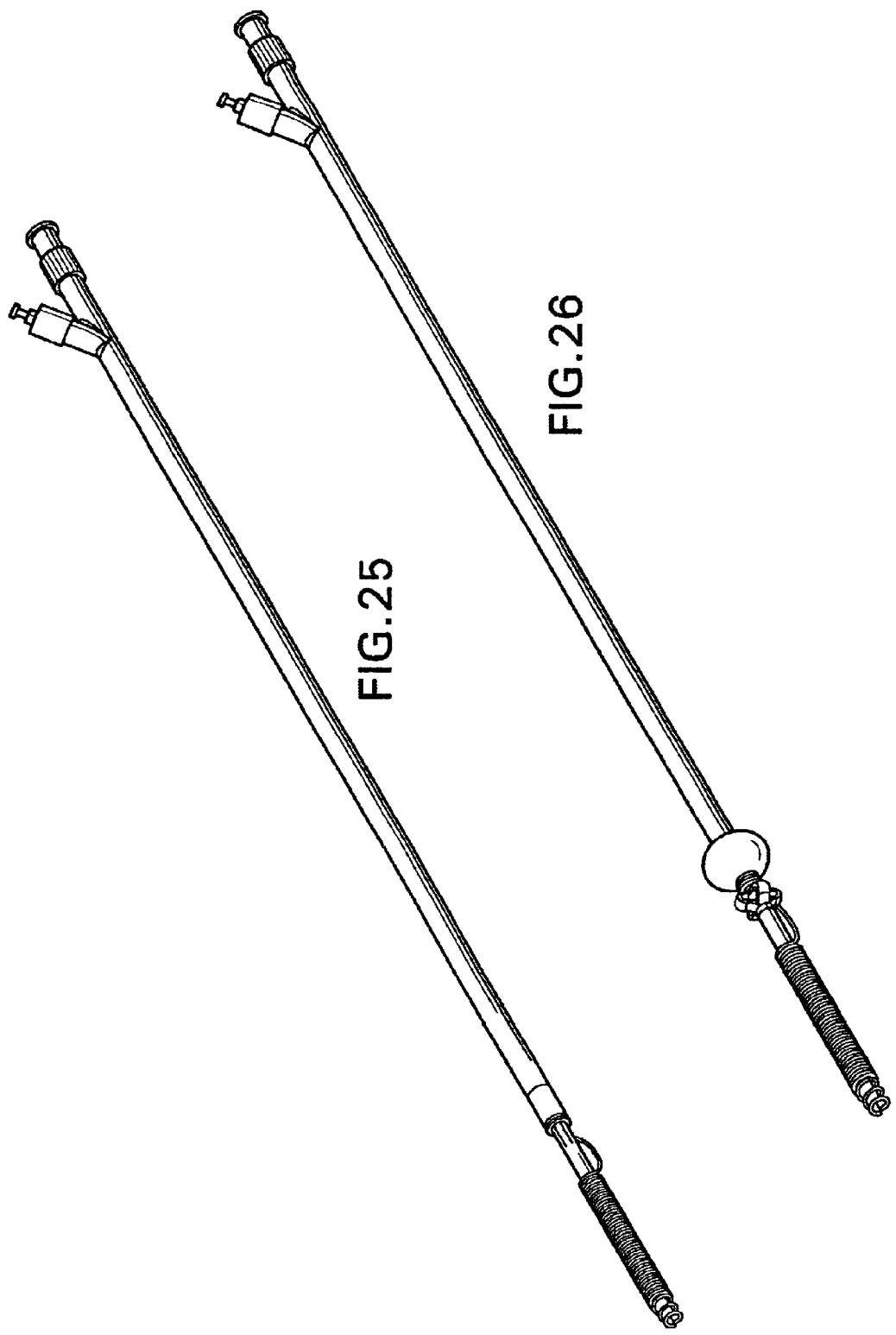

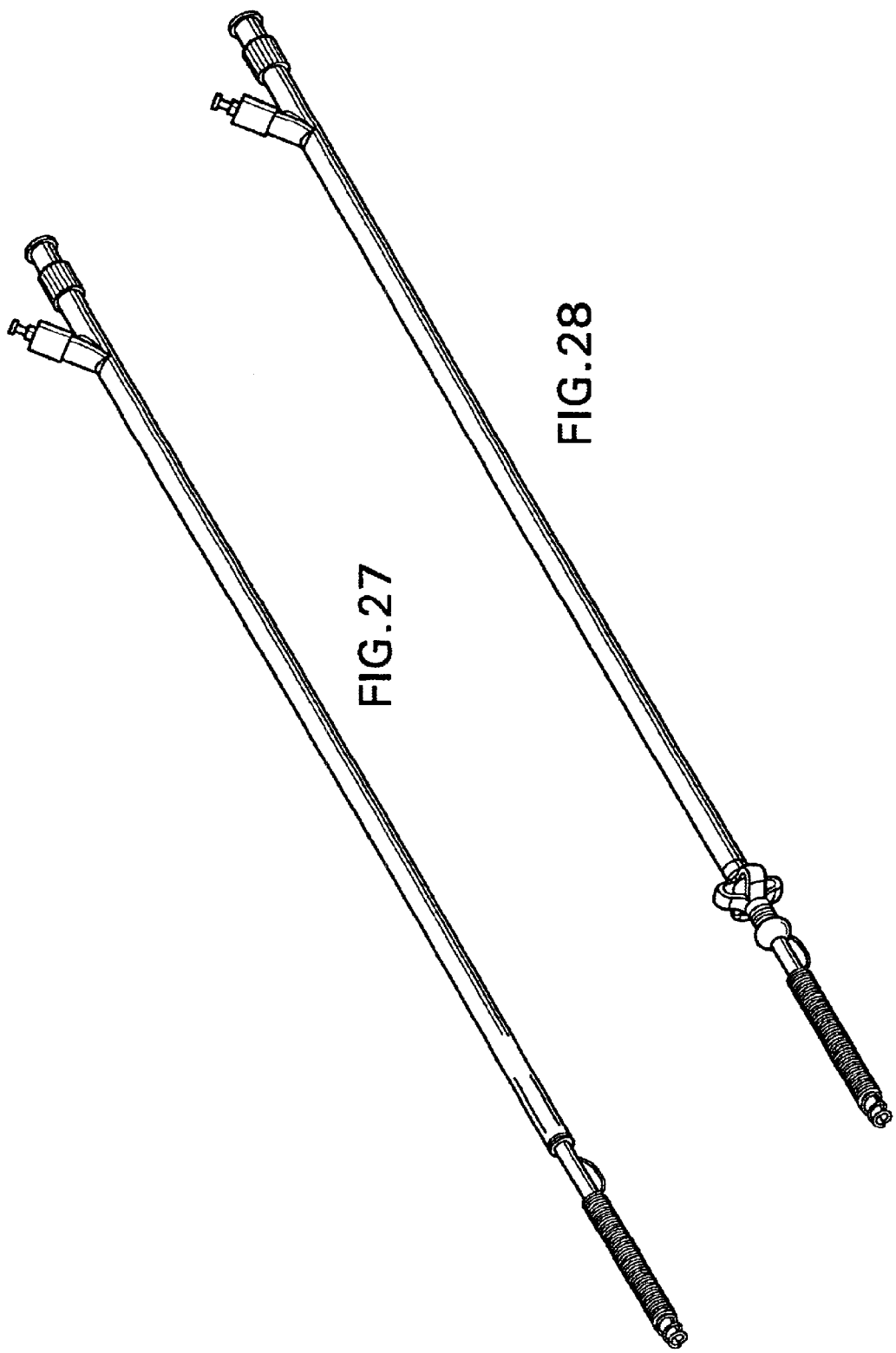

URETHRAL STENT DELIVERY SYSTEM

FIELD OF THE INVENTION

The invention relates to the field of treatment of body cavities with stents, for instance urological stents, and more particularly to such stents which are used in the treatment of prostatic hyperplasia.

More specifically, in order to fullfill the needs of beneficial treatment, the present invention relates to a device for inserting and/or locating a stent in a body cavity, especially the prostatic stent in a human male urethra to treat the prostatic hyperplasia therein. It also is possible to utilize the device of the present invention for the placing of stents in other body cavities, such as the esophagus, the biliary passage, the intestine, or the trachea.

BACKGROUND OF THE INVENTION

Prostatic stents are used to keep the prostatic lobes apart, preventing the compression of the urethra and allowing free urinary flow after different types of prostatic thermal therapy methods (e.g., VLAP, TUMT, TULIP, ILC, TUNA, HIFY, cryosurgery etc.) have been utilized to treat benign prostatic hyperplasia. Such stents may also be used in provisional treatment of patients with urinary retention who are waiting for prostatic surgery or to test the effect of surgical treatment in the case of lower urinary tract obstruction induced by benign prostatic hyperplasia. As the oedema subsides, the stent can be withdrawn. If the stent material is bioabsorbable, the prostatic stent gradually loses its strength after a determinate time period, and the small fragments of the stent exit the body through urea.

Devices for placing stents in, e.g., male urethra, are known in the prior art, for instance, from U.S. Pat. No. 5,098,374 to Othel-Jacobsen ("the '374 patent") and U.S. Pat. No. 5,160,341 to Brenneman, the entire disclosures of which are incorporated herein by way of this reference. A considerable disadvantage in the prior art devices is that the correct location of the inserting device and thus the location of the stent to be placed inside the body cavity is not known. Thus, when using such prior art devices, a visualization method such as ultrasound, magnetic resonance or direct visual contact is needed to ensure the correct location of the stent in the body cavity during or after the insertion. It is a purpose of the present invention to overcome this deficiency of the prior art.

SUMMARY OF THE INVENTION

It is an object of the present invention to provide a device for inserting a stent in a body cavity, such as the prostate via the urethra. The device may comprise an outer elongate tubular mantle having first and second ends, and an elongate member placed inside the mantle, having first and second end portions protruding form the respective ends of the mantle. Further, the device may comprise means for preventing said stent from sliding off of the member, and means for locating an obstacle in the body cavity.

Broadly, the device of the present invention is used as an applicator for inserting a stent into a body cavity, especially a urethral stent into the prostatic area. The stent can be made of biodegradable or bioresorbable material or biostable materials, such as stainless steel or plastic. Stents suitable for use with the invention can be in the form of, e.g., a single or multiple helical coil, or knitted tubular mesh or solid tube with holes or cuts around the tube wall. In a preferred embodiment of the present invention, the insertion device includes means for preventing the stent from sliding off of the insertion device, means for inserting the stent into, e.g., the prostatic urethra, and means for stopping the insertion of the stent and the device at, e.g., the sphincter, whereby the distal end of the stent is left in the bulbous urethra.

The stent may be released from the device in the selected location in the urethra and is left there, relieving the prostatic hyperplasia.

The device of the present invention solves problems present in insertion devices of the prior art, such as that of the '374 patent, which requires ultrasound analysis (suprapubic or transrectal) during the insertion of the stent to localize the stent. Such localization techniques are not exact because, e.g., if the patient could not void or was incontinent after stent insertion, then cystoscopy is necessary to ensure the exact location of the stent. However, in the present invention, a balloon or cut strips (see below) divide the insertion catheter, making stent localization possible without the risk of additional cystoscopy.

BRIEF DESCRIPTION OF THE DRAWINGS

FIG. 1 shows a perspective view of a first embodiment of the device of the invention with a preinstalled stent, FIG. 2 shows the device of FIG. 1 with a stent, FIG. 3 shows a perspective view of the tubular, cannula-like mantle, FIG. 4 shows a perspective view of the elongated member, which is placed inside the mantle of FIG. 3, together with means for controlling the movements of the elongated member, FIG. 5 shows a perspective view of the elongated member and the means for controlling the movements of the elongated member of FIG. 4 in a position where the means for holding the stent on the device are activated, FIG. 9 shows a perspective view of a second embodiment of the device of the invention with a fastened stent, FIG. 10 shows the device of FIG. 9 with means for locating an obstacle in a body cavity activated, FIG. 11 shows a perspective view of the tubular mantle of FIGS. 9 and 10 with the means for locating an obstacle in a body cavity inactivated, FIG. 12 shows a perspective view of the tubular mantle of FIG. 11 where the means for locating an obstacle in a body cavity is activated, FIG. 13 shows a perspective view of the elongated member, which is placed inside the mantle of FIGS. 11 and 12.

FIGS. 17–28 depict perspective views of additional embodiments of the invention comprising various combinations of the embodiments depicted in the foregoing Figures.

DETAILED DESCRIPTION OF THE PREFERRED EMBODIMENTS OF THE INVENTION

Figure 6:
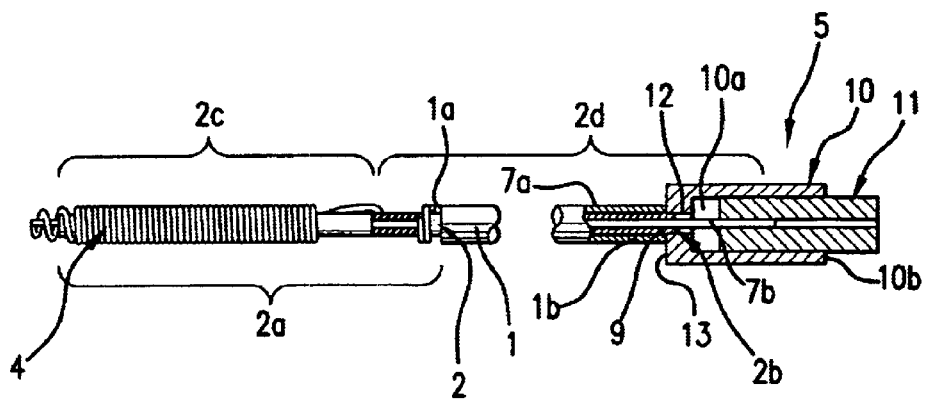
FIG. 6 shows a plan view of the device of FIG. 1 with partial cross-section.

Referring now to FIGS. 1–8, in which a first embodiment of the device of the invention is illustrated, the device comprises as main components a mantle 1, an elongated member 2, fastening elements 3 for the stent 4, control means 5 and sensing means 6.

Figure 8:
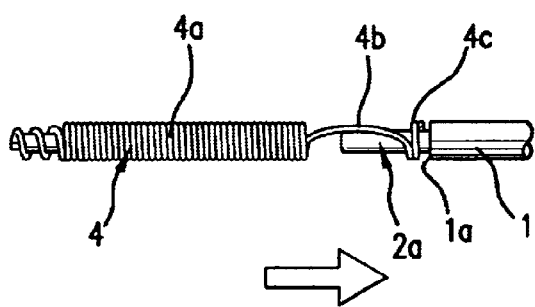
FIG. 8 shows a plan view of the device seen from the direction similar to FIGS. 6 and 7 in the phase where the stent is loosened for release from the end of the device.

The length of the mantle 1 is such that the front end of the mantle 1 can reach the area of the sphincter before the prostate when the device is inserted into the male urethra via the external urethral orifice. The stent 4 is fastened in accordance with FIG. 2 to the first front end portion 2a of the elongated member 2. The outer dimensions of the tubular mantle 1 and stent 4 are selected in a manner that they can easily be brought into the male urethra. The control means 5 are outside the external urethra orifice when the stent 4 is installed, so that when the stent 4 is loosened for release from the device, as shown in FIG. 8, the control means 5 may be easily manipulated manually.

Figure 7:
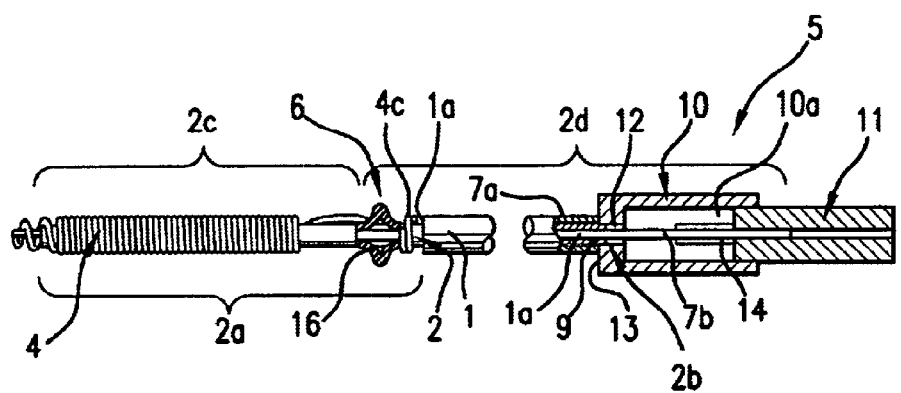
FIG. 7 shows a plan view of the device of FIG. 2 with partial cross-section.

The elongated member 2 shown in FIGS. 6 and 7 is longer than the mantle 1 thereby having first and second end portions 2a, 2b protruding from the respective ends of the mantle 1. The first, front end portion 2a is substantially placed inside the stent 4, which in this embodiment is designed as a helical coil. Further, the elongated member 2 is divided into two sections 2c, 2d, which in one embodiment of the present invention have approximately the same diameter. In the embodiment shown in FIGS. 6 and 7, the first section 2c of the elongated member 2 has unitary construction and is formed as a stick-like element in connection with the front end portion 2a. The distal part of the front end portion 2a of the elongated member 2 is outside the front end of the mantle 1, which itself is divided into a second section 2d by a division of the unitary construction of the first section 2c into an outer tubular means 7a and an inner elongated means 7b, which resides inside said outer tubular means 7a. The outer tubular means 7a are provided with cuts, e.g., 8a, 8b in FIG. 1. Said cuts protrude from the outer tubular means 7a in the longitudinal direction. Those cuts (four of which are presented in the first embodiment of the device shown in FIGS. 1–8) are equidistantly divided around the periphery of the outer tubular means 7a. The cuts have their distal end at the point of the division between the first and second sections, 2c and 2d. The proximal end of the cuts is settled at a certain distance from the front end 1a of the mantle 1, so that the stent 4 can be attached to the device as explained in more detail below.

Means 5 for controlling the movements of the elongated member are affixed to the rear, second end portion 2b of the elongated member 2. The main parts of the control means 5 are a sleeve 10 and slide means 11 therein. As shown in FIGS. 1–8, especially in FIGS. 6 and 7, the rear end part 9 of the outer tubular means 7a together with the rear end part 1b (FIG. 6) of the mantle 1 are fixed to the front end wall 13 of the sleeve 10, and the inner elongated means 7b is fixed to the front end of the slide means 11. The inner elongated means 7b is arranged to go through the hole 12 in the front end wall 13 of the sleeve 10 and inside the hole 10a of the sleeve 10, wherein the slide means 11 is arranged to be moved manually in relation to the sleeve 10 in the longitudinal direction of the device. With reference to the embodiment of FIGS. 1 and 2, the sleeve 10 has at a longitudinal wall a longitudinal groove 14 which opens towards the rear end of the sleeve 10. The slide means 11 is provided with an elevation 15 which is positioned into the groove 14, as shown in FIG. 1. Further, the slide means 11 is provided with a handle part 16 protruding from the rear end of the sleeve 10, the handle preferably including a prepared surface for manual gripping and using the control means 5.

As for the stent 4 (FIG. 8), it comprises an elongated, coiled wire part 4a to be placed at the area of the prostate, a longitudinal rod part 4b connected to the elongated wire part 4a from the first end of the same and to be placed into a body cavity, such as at the area of sphincter muscle of urethra, and further a coiled locking part 4c connected to the second end of the longitudinal rod part for placing in the urethra in front of the sphincter muscle. The stent 4 is preferably made of a bioabsorbable polymer material.

In the embodiment of FIGS. 1–8, to install the stent 4 on the device for further insertion into a body cavity, the stent 4 is pushed onto the first portion 2a of the elongated member 2 in a manner that the rear end of the stent, i.e., the locking part 4c, passes the cuts, e.g., 8a, 8b, in the longitudinal direction of the elongated member 2. Thus, the locking part 4c is located in the area of the elongated member 2 between the cuts and the front end part 1a of the mantle 1. This phase of attaching the stent to the device is shown in FIGS. 1 and 6. By pulling the slide means 11 out of the hole 10a of the sleeve 10 and by turning the slide means 11 around the longitudinal axis of the device, the front end 15a of the elevation 15, which has passed by the rear end 10b of the sleeve 10, is brought against said rear end 10b, thereby activating the locating means 6 at the cuts (e.g., 8a, 8b). This activation is due to the shortening of the distance between the front end of the second section 2d and the front end wall 13 of the sleeve 10, which is effected by the pulling the inner elongated means 7b as described above. Such shortening causes the strips 16 (FIG. 4) between the cuts (e.g., 8a, 8b) to bend radially outwards at their middle sections. Thus, the locking part 4c of the stent 4 is locked between the outwardly bending strips 16 (FIGS. 5 and 7) and the front end part 1a of the mantle 1, and simultaneously the strips 16, form wing-like locating means 6 just ahead of the locking part 4c projecting radially outwards from the outer surface of the device.

The locating means 6 is used to locate the correct position of the stent 4, by preventing the locking part 4c of the stant from progressing past, e.g., the sphincter muscle. When the stent 4 is at the correct position, the slide means 11 is brought back to the position shown in FIGS. 1 and 6, whereby the strips 6 are again lying in the longitudinal direction of the device, thereby releasing the locking part 4c of the stent from the locked position. Simultaneously, the first position 2a of the elongated member 2 is free to be retracted from the interior of the same, as shown in FIG. 8, and further the device can be retracted from the urethra.

Figure 14:
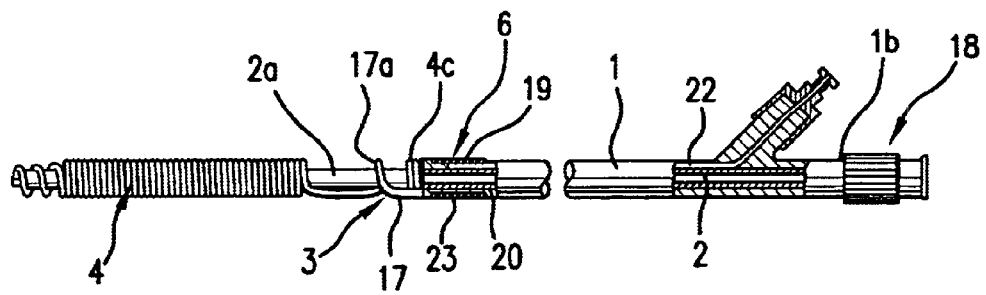
FIG. 14 shows a plan view of the device of FIG. 9 with partial cross-section.
Figure 15:
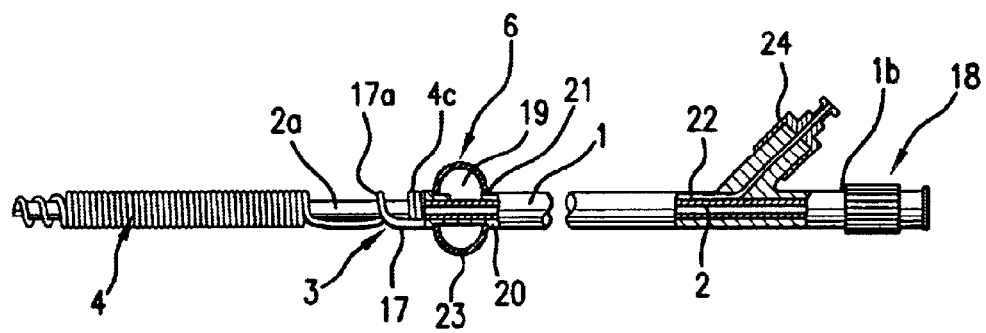
FIG. 15 shows a plan view of the device of FIG. 10 with partial cross-section.
Figure 16:
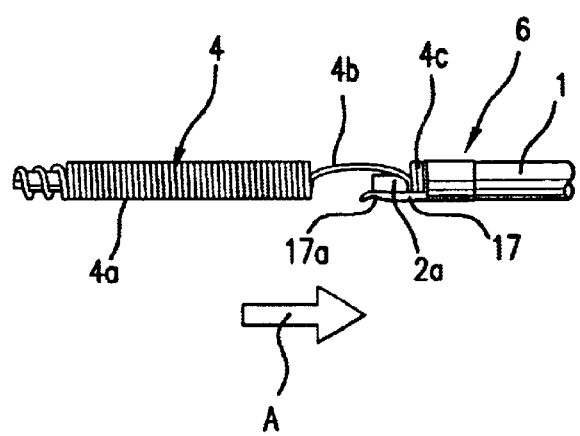
FIG. 16 shows a plan view of the device seen from the direction similar to FIGS. 14 and 15 in the phase where the stent is loosened for release from the end of the device.

A second embodiment of the invention is shown in FIGS. 9–16. The device has the same main components as the first embodiment shown in FIGS. 1–8. In the second embodiment of the invention, the mantle 1, which in the first embodiment is constructed as a single tube, is (as especially seen in FIG. 11) comprised of a locating means 6 and a ring-shaped member 17 protruding from the first end 1a of the mantle 1. Further, the elongated member 2 is constructed as a single, stick-like element, as shown in FIG. 13, having a first front end portion 2a protruding from the first end 1a of the mantle 1 inside the stent 4 in a similar manner as explained in connection with the first embodiment above. With reference to FIGS. 9 and 10, the elongated member 2 is shown penetrating through the hole 17a of the ring-shaped member 17 when the stent 4 is locked in connection with the device. The first front section 2a of the elongated member 2 passes through the hole 17a of the ring-shaped member 17, forming a closed ring that locks the coiled locking part 4c of the stent 4 inside the said closed ring. By retracting the elongated member backwards, as shown in FIG. 16 (arrow A), the closed ring is opened when the the ring-shaped member 17 is released from connection to the elongated member 2. In this way, the locking part 4c and the whole stent 4 is freed from the insertion device. For purposes of the insertion and retraction of the elongated member 2, the rear end of that member is equipped with a handle and locking part 18, which is fastened frictionally to the rear end 16 of the mantle 1 when the elongated member 2 is inserted into the mantle 1 and the stent 4 is fastened to the device.

The locating means 6 are placed at the front end of the mantle 1, as shown in FIGS. 14 and 15, at a space 19 having its expansion limited by a section 20 of the surface of the mantle 1. The section 20 is provided with at least one aperture 21 connected by a tubular line 22 inside the mantle 1 to the second rear end 1b of the mantle 1. The tubular line 22 is provided for transfer of a pressure medium to and from the space 19. A tubular elastic member 23, like a balloon, is overlying said section 20 of the surface of the mantle 1 and is fastened tightly from both ends of said tubular elastic member 23 onto the surface of the mantle 1, around the periphery of the same. An adapter 24 is fixed in connection with the mantle 1 at the rear end 1b of the same and at the rear end of the tubular line 22 for providing and releasing the pressure medium to and from the space 19.

The second embodiment can be used in a similar manner as explained above in connection with the first embodiment of the invention. The balloon-like locating means 6 is expanded as shown in FIG. 15 to locate the correct position of the stent 4. After locating that correct position, the locating means 6 is deflated and the elongated member 2 is retracted, as shown in FIG. 16, whereby the stent 4 is released due to the opening of the closed ring. The device can be retracted from the urethra after the stage shown in FIG. 16.

In the above embodiments, the locating means (balloon or cut strips or equivalent) is used to hold the stent onto the device and to localize the stent within the body cavity, thereby simplifying the device, making it easy for a surgeon to handle and reducing its risk in use during surgery. Further, unlocking the stent from the device is simple and easy, making stent placement within the body cavity more precise and exact. Indeed, only a half-turn of the tube is necessary to release the stent (or deflate the balloon), as compared to the more burdensome release techniques of the prior art, such as the device of the '374 patent (requiring several turns to release the stent). The outer tube of the insertion device may be made from a material that is rigid or semi-rigid, thereby facilitating stent placement, location and unlocking from the device.

FIGS. 17 and 18 show yet another embodiment of the device in which the cuts (e.g., 8A,8B) are made onto the mantle 1 at the front end of the same in a similar manner as described above. A cord (not shown) may be led thorough the mantle 1 in a manner that a loop is provided which locks the locking part 4c of the stent 4, and thus the whole stent, in connection with the insertion device. Both ends of the cord may be fixed to the slide means 11. When the slide means 11, starting from the position shown in FIG. 17, is pulled and turned as described above the locking part 4c forces the cuts (e.g., 8A,8B) to bend outwards to form the locating means 6A as shown in FIG. 18.

FIGS. 19 and 20 show yet another embodiment of the invention, comprising a combination of the embodiments of FIGS. 1 and 2 with that of FIGS. 17 and 18. The function of this embodiment of the device can be understood on basis of the teachings given in connection with the corresponding parts of the specification above. The outer tubular means 7a are provided with first cuts (e.g., 8a, 8b), said first cuts protruding from the outer tubular means 7a in the longitudinal direction of the outer tubular means 7a. Second cuts (e.g., 8A,8B) also are made onto the mantle 1 at the front end of the same in a similar manner as the first cuts. When the slide means 11, starting from the position shown in FIG. 19 is pulled, the first cuts (e.g., 8a,8b) lock the locking part 4c of the stent 4, thus providing a first locating means 6a as described in connection with FIGS. 1 and 2. Then the second cuts are bent outwards due to the continued movement of the first locating means 6a together with the locking part 4c towards the sleeve 10, thus forming the second locating means 6A. When inserting this embodiment of the device, the first locating means 6a meets the sphincter muscle of the urethra and the stent 4 can be released as described above.

FIGS. 21 and 22 show another embodiment of the invention, in which the balloon 6a fastens the stent 4 in place of the wing construction of the embodiment shown in FIGS. 1 and 2. The locating means of this embodiment are formed onto the surface of the outer tubular means 7a of the elongate member 2. When the balloon 6a meets the sphincter muscle of the urethra, the stent 4 can be released by emptying the pressure in the expanding space.

FIGS. 23 and 24 show another embodiment of the invention comprising a partial combination of the embodiment of FIGS. 9 and 10, together with the embodiment of FIGS. 21 and 22. In this embodiment of the invention, the first balloon 6a is formed onto the surface of the outer tubular means 7a of the elongated member 2, and the second balloon 6A is formed onto the surface of the mantle 1. FIGS. 25 and 26 depict yet another embodiment of the invention, which is a partial combination of embodiments shown in FIGS. 1 and 2 with that of FIGS. 9 and 10. Likewise, FIGS. 27 and 28 show an additional embodiment of the invention, which is a partial combination of the embodiment shown in FIGS. 21 and 22 with that of FIGS. 17 and 18.

We claim:

1. A device for inserting a stent in a body cavity, said device comprising:
    an outer elongated mantle having first and second ends;
    an elongated member movably located inside said mantle, said member having first and end portions protruding from said respective ends of said mantle, said first end portion of said member being capable of removably receiving said stent; and
    means for locating the position of an obstacle in said body cavity.

2. The device of claim 1 wherein said stent is temporarily prevented from sliding off said member by said locating means.

3. The device of claim 1 wherein said locating means projects radially outward from said member.

4. The device of claim 1 wherein said locating means projects radially outward from said mantle.

5. The device of claim 1 wherein said locating means comprises a balloon that is capable of temporarily protruding outward from said member.

6. The device of claim 1 wherein said locating means comprises a balloon that is capable of temporarily protruding outward from said mantle.

7. The device of claim 1 wherein said stent is temporarily prevented from sliding off said member by a cord.

8. A device for inserting a stent in a body cavity comprising:

an outer elongated mantle having first and second ends;

an elongated member movably located inside said mantle, said member having first and second portions protruding from said respective ends of said mantle, said first end portion of said member being capable of removably receiving said stent;

said mantle comprising a balloon capable of temporarily protruding from said mantle.

9. The device of claim 8 further comprising a ring attached to said first end of said mantle for removably receiving said member, wherein said member may be advanced through a portion of said stent, through said ring, and through another portion of said stent so that a portion of said stent is located on either side of said ring.

10. A device for inserting a stent in a body cavity comprising:

an outer elongated mantle having first and second ends;

an elongated member movably located inside said mantle, said member having first and second portions protruding from said respective ends of said mantle, said first end portion of said member being capable of removably receiving said stent;

said mantle comprising a ring attached to said first end of said mantle for removably receiving said member, wherein when said member may be advanced through a portion of said stent, through said ring, and through another portion of said stent so that so that a portion of said stent is located on either side of said ring.

\* \* \* \* \*